(12) United States Patent
Zhou et al.

(10) Patent No.: US 6,919,065 B2
(45) Date of Patent: Jul. 19, 2005

(54) SUPPORTED NOBLE METAL, PHASE-CONTROLLED CATALYST AND METHODS FOR MAKING AND USING THE CATALYST

(75) Inventors: Bing Zhou, Cranbury, NJ (US); Lap-Keung Lee, West Windsor, NJ (US)

(73) Assignee: Hydrocarbon Technologies, Inc., Lawrenceville, NJ (US)

(*) Notice: Subject to any disclaimer, the term of this patent is extended or adjusted under 35 U.S.C. 154(b) by 176 days.

(21) Appl. No.: 10/431,693

(22) Filed: May 7, 2003

(65) Prior Publication Data

US 2003/0232004 A1 Dec. 18, 2003

Related U.S. Application Data

(63) Continuation of application No. 09/867,190, filed on May 29, 2001, now Pat. No. 6,576,214, which is a continuation-in-part of application No. 09/733,154, filed on Dec. 8, 2000, now Pat. No. 6,500,968, which is a continuation-in-part of application No. 09/140,265, filed on Aug. 26, 1998, now Pat. No. 6,168,775.

(51) Int. Cl.[7] .................. C01B 15/01; B01J 21/18; B01J 21/08; B01J 21/12; B01J 23/00
(52) U.S. Cl. .................. 423/584; 502/184; 502/185; 502/243; 502/258; 502/261; 502/262; 502/325; 502/326; 502/327; 502/333; 502/334; 502/339; 502/344
(58) Field of Search .................. 502/184, 185, 502/243, 258, 261, 262, 325, 326, 327, 333, 334, 339, 344; 423/584

(56) References Cited

U.S. PATENT DOCUMENTS

| | | |
|---|---|---|
| 4,007,256 A | 2/1977 | Kim et al. |
| 4,028,274 A | 6/1977 | Kunz |
| 4,128,627 A | 12/1978 | Dyer et al. |
| 4,335,092 A | 6/1982 | Dalton et al. |
| 4,336,239 A | 6/1982 | Dalton et al. |
| 4,336,240 A | 6/1982 | Moselay et al. |

(Continued)

FOREIGN PATENT DOCUMENTS

| | | |
|---|---|---|
| EP | 0864362 | 9/1998 |
| EP | 0978316 | 2/2000 |
| WO | WO 98/10863 | 3/1998 |

OTHER PUBLICATIONS

"Shape–Controlled Synthesis of Colloidal Platinum Nano-particles" by T. Ahmadi et al, Science, vol. 272, Jun. 28, 1996, pp. 1924–1926.

*Primary Examiner*—Cam N. Nguyen
(74) *Attorney, Agent, or Firm*—Workman Nydegger (57) ABSTRACT

A particulate supported noble metal phase-controlled catalyst material having 5–1000 $\mu$m surface area of 50$\mu$500 m$^2$/gm is provided for use in direct catalytic production of hydrogen peroxide ($H_2O_2$) product from hydrogen and oxygen-containing feedstreams. The catalyst is made by depositing phase controlled crystals of a noble metal such as palladium on a suitable particulate support material such as carbon black, by utilizing a precursor solution of the metal and a suitable control ionic polymer having molecular weight of 300–8000 such as sodium polyacrylate in a selected metal to polymer molar ratio of 1:0.1 to 1:10, which procedure provides desired phase control of the noble metal atoms to form widely dispersed minute noble metal crystals on the support material. The invention includes methods for making the catalyst, and also a process for utilizing the catalyst to directly produce high yields of hydrogen peroxide ($H_2O_2$) product from hydrogen and oxygen-containing gaseous feedstreams.

46 Claims, 3 Drawing Sheets

SCHEMATIC PRESENTATION OF $H_2/O_2$ REACTION ON PALLADIUM ATOM

U.S. PATENT DOCUMENTS

| | | |
|---|---|---|
| 4,347,231 A | 8/1982 | Michaelson |
| 4,347,232 A | 8/1982 | Michaelson |
| 4,476,242 A | 10/1984 | Puskas et al. |
| 4,701,428 A | 10/1987 | Bellussi et al. |
| 4,713,363 A | 12/1987 | Hucul |
| 4,824,976 A | 4/1989 | Clerici et al. |
| 4,937,216 A | 6/1990 | Clerici et al. |
| 4,937,220 A | 6/1990 | Nickols, Jr. |
| 5,024,905 A | 6/1991 | Itoh et al. |
| 5,061,671 A | 10/1991 | Kitson et al. |
| 5,096,866 A | 3/1992 | Itoh et al. |
| 5,104,635 A | 4/1992 | Kanada et al. |
| 5,166,372 A | 11/1992 | Crocco et al. |
| 5,214,168 A | 5/1993 | Zajacek et al. |
| 5,338,531 A | 8/1994 | Chuang et al. |
| 5,372,981 A | 12/1994 | Witherspoon |
| 5,399,344 A | 3/1995 | Yang et al. |
| 5,698,488 A | 12/1997 | Birbara et al. |
| 5,767,036 A | 6/1998 | Freund et al. |
| 5,900,386 A | 5/1999 | Freund et al. |
| 5,912,367 A | 6/1999 | Chang |
| 5,961,948 A | 10/1999 | Wanngard |
| 5,965,101 A | 10/1999 | Goto et al. |
| 6,090,858 A | 7/2000 | El-Sayed |
| 6,159,267 A * | 12/2000 | Hampden-Smith et al. ... 75/252 |
| 6,168,775 B1 | 1/2001 | Zhou et al. |
| 6,194,338 B1 | 2/2001 | Andolfatto et al. |
| 6,284,213 B1 | 9/2001 | Paparatto et al. |
| 6,500,968 B2 | 12/2002 | Zhou et al. |
| 6,518,217 B2 | 2/2003 | Xing et al. |
| 6,534,661 B1 | 3/2003 | Zhou et al. |
| 6,576,214 B2 | 6/2003 | Zhou et al. |
| 6,635,348 B1 * | 10/2003 | Hampden-Smith et al. . 428/402 |

\* cited by examiner

SCHEMATIC PRESENTATION OF $H_2/O_2$ REACTION ON PALLADIUM ATOM

FIG. 1 a. (110)   b. (100)   c. (111)

SCHEMATIC PRESENTATION OF $H_2/O_2$ REACTION ON PALLADIUM ATOM

○ FIRST LAYER   ◎ SECOND LAYER   ● THIRD LAYER

SUPPORTED NOBLE METAL, PHASE-CONTROLLED CATALYST AND METHODS FOR MAKING AND USING THE CATALYST

CROSS-REFERENCE TO RELATED APPLICATIONS

This application is a continuation of U.S. application Ser. No. 09/867,190, filed May 29, 2001, now issued as U.S. Pat. No. 6,576,214, which is a continuation-in-part of U.S. application Ser. No. 09/733,154, filed Dec. 8, 2000, now issued as U.S. Pat. No. 6,500,968, which is a continuation-in-part of U.S. application Ser. No. 09/140,265, filed Aug. 26, 1998, now issued as U.S. Pat. No. 6,168,775. The foregoing applications are incorporated herein by reference in their entirety.

BACKGROUND OF THE INVENTION

1. The Field of the Invention

This invention pertains to production hydrogen peroxide ($H_2O_2$) by direct catalytic synthesis using hydrogen and oxygen-containing feedstreams. It pertains particularly to a supported noble metal phase-controlled catalyst having high activity and product selectivity, and which is useful for such direct hydrogen peroxide production process utilizing feedstreams having hydrogen concentration less than about 4% by volume.

2. The Relevant Technology

Demand for hydrogen peroxide product has been growing globally at about 6% annually, and in North America at about 10% annually. Such demand growth is due primarily to the environmental advantages of hydrogen peroxide usage, which upon decomposition releases only oxygen and water. Hydrogen peroxide is an effective replacement for chlorine in pump and paper bleaching, water treatment and other environmental processes, and meets the growing product demand and need for a simple environmentally friendly and cost effective process that can be located on-site for the pulp, paper and other manufacturing facilities. The hydrogen peroxide presently being produced commercially uses a known anthraquinone process which has low yields and some safety problems. Also, transportation of hydrogen peroxide from a production site to an end-user facility is an important safety issue due to the risk of explosion of hydrogen peroxide by its violent decomposition.

Many attempts have been made to produce hydrogen peroxide directly from hydrogen and oxygen-containing feedstreams, because such a process not only has potential for significantly reducing the production cost, but also provides an alternative production process which avoids the present user of toxic feedstock and working solutions. For such direct catalytic production of hydrogen peroxide, the feedstreams are hydrogen and air which are clean and environmentally harmless, and no organic solvent is used in such a direct synthesis process. The reaction medium is water, and the hydrogen peroxide formed does not contain any organic compounds. Such direct process generates no waste and is cost efficient due to its inherent simplicity and the hydrogen peroxide product can e used directly as a bleaching agent in pulp and paper processes. However, such proposed direct production technology has not yet been commercialized, as the major problems for the known processes are (1) hazardous operating conditions (with the feed hydrogen partial pressure above an explosive range), (2) low reaction rates, and (3) low catalytic product selectivity.

Although the direct catalytic synthesis of hydrogen peroxide product has attracted much attention and many patents have been issued, none of the patented processes have been commercially feasible due to low catalyst activity and the low selectivity for the production of hydrogen peroxide. Until the early 1990's, most of these patents utilized as feed gas at least 10% hydrogen in air or oxygen, which is within the explosion limits for the $H_2/O_2$ mixture. Due to increasing safety concerns, the recent approach has been to utilize feedstreams having hydrogen concentration below about 5 vol. %. However, at such low hydrogen concentration, the catalysts used must be much more active to achieve an acceptable production rate of hydrogen peroxide. Highly dispersed palladium on various support materials has been used to enhance the catalytic activity. However, the dispersion methods used have not adequately controlled the crystal phase of the palladium, and desired improvement in selectivity towards hydrogen peroxide product has not been achieved. A main problem in preparing a highly selective catalyst for hydrogen peroxide production is how to consistently control the formation of a desired metal phase such as phase 110 or 220, etc. in the catalyst.

Such known prior attempts to develop a commercial hydrogen peroxide process are described in various patents. For example, U.S. Pat. No. 4,661,337 to Brill discloses producing hydrogen peroxide by decently reacting hydrogen and oxygen at superatomospheric pressure in an acidic aqueous solution containing a suspended catalyst formed of a layer of supported noble metal such as palladium. U.S. Pat. No. 4,681,751 to Gosser discloses a catalytic process for making hydrogen peroxide from hydrogen and oxygen using as catalyst palladium on small carbon support particles in an aqueous medium containing an acid component and halide ion component. U.S. Pat. No. 4,722,458 to Gosser et al. discloses a similar process which used as catalysts Pd alone or a Pd and Pt mixture on various carriers in an aqueous reaction medium containing a bromide promoter. U.S. Pat. No. 4,832,938 to Gosser et al. discloses a similar direct hydrogen peroxide production process using platinum/palladium catalysts. U.S. Pat. No. 5,236,692 to Nagashimia et al. discloses a method for producing hydrogen peroxide by directly reacting hydrogen and oxygen in a medium containing a promoter and using a platinum group metal catalyst supported on a solid superacid carrier. U.S. Pat. No. 5,378,450 to Tomita et al. describes a process using a supported tin-modified palladium as catalyst, in a liquid medium containing no halogen ions. U.S. Pat. No. 5,399,334 to Kawakami et al. disclosed a direct hydrogen peroxide process using an aqueous medium containing an organic solvent and as catalyst palladium supported on alumina, silica or activated carbon for product selectivity ranged between 55% an 82%. Also, U.S. Pat. No. 5,338,531 to K. Chuang et al. disclosed a direct catalytic process using a feed gas containing 3.2 vol. % oxygen; 10 vol. % nitrogen and 86.8% vol. oxygen, product selectivity ranged between 38% to 100%, but deceased with increased catalyst age. The catalyst support was hydrophobic fluorinated carbon which is very expensive and has not been produced commercially in large quantity. Also, in these patented processes, the catalysts were apparently tested for only a short time.

Based on the above catalyst development activity and inferior results, it is apparent that to provide a direct catalytic hydrogen peroxide process that is commercially feasible, it is necessary to modify the noble metal structure of the catalyst so that its activity at low hydrogen concentration and partial pressure remains substantial, and also so that the catalyst is stable over sufficiently long periods of time essential for successful commercial production operations.

SUMMARY OF INVENTION

This invention provides an improved particulate supported noble metal catalyst which is very useful for direct catalytic production of hydrogen peroxide ($H_2O_2$) product from hydrogen and oxygen containing feedstreams, and also provides a direct hydrophobic peroxide production process utilizing the catalyst. The catalyst is formed by utilizing a colloid solution of a suitable active noble metal and a control ionic polymer for dispersing atoms of the active metal component onto a particulate support material having a critical large surface area. This catalyst not only utilizes the active noble metal being highly dispersed minute crystal form on the support materials, but also has controlled exposition of the crystal phase(s) of the noble metal on the support by utilizing the controlling ionic polymer in a critical molar ratio of the noble metal to the polymer in the broad range of 1:0.1 to 1:10 depending on the molecular weight of the polymer. The selective exposition of specific desired crystal phases or faces of the noble metal on the support has been found to be a critical factor for improvement of the catalyst and its activity and product selectivity for directly producing the hydrogen peroxide product, because the hydrogen-oxygen catalytic reaction is sensitive to the exposed phase(s) of the minute noble metal crystal particles in the catalyst. The resulting catalyst utilizing a phase controlled noble metal crystal practical has high catalytic activity and product selectivity, which permits the use of lower safe hydrogen concentrations (below LEL 4% relative) to the oxygen or to the air in the feedstream for making hydrogen peroxide product.

Suitable catalyst support materials include alumina, activated carbon, carbon black and silica powders having particle size of 5–1,000,000 nanometers (nm) and preferably $m^2/gm$, with carbon black being preferred. Noble metals which are useful for this catalyst include palladium (Pd), platinum (Pt), gold (Au), iridium (Ir), osmium (Os), rhodium (Rh), or ruthenium (Ru), and combinations thereof with the preferred metal s being palladium and platinum. Useful broad percentage concentration for the noble metal in the catalyst is 0.1–10 wt. %, with 0.2–5 wt. % range usually being preferred. The noble metal minute crystals each have a particle size of 1–100 nanometers (nm). Suitable ionic polymers should be either negatively charge or have a lone pair of electrons that can attract the metal positively charge ions such as $Pd^{2+}$, and also have molecular weights within the range of about 300–8000 and preferably 600–6000. Examples of suitable polymers include polyacrylates, polyvinyl benzoates, polyvinyl sulfate, polyvinyl sulfonates, polybiphenol carbonates, polybenzimidozoles, and polypyridines, and other polymer agents having similar molecular structures. The desired molar ratio of the noble metal to the polymer is generally dependent on the molecular weigh to of the polymer, with the higher range ratios being required for those polymers having higher molecular weights.

The catalyst of this invention which provides for the direct synthesis of hydrogen peroxide ($H_2O_2$) product from hydrogen and oxygen-containing feedstreams has minute particles of the noble metal such as palladium deposited as crystals having a critical phase or phases on the support material having selected critical surface area of 50–500 $m^2/gm$, such as activated carbon or carbon black. The desired noble metal phase exposition or structure for this catalyst is formed by utilizing the controlling ionic polymer, for example sodium polyacrylate in the critical ratio with the active noble metal such as palladium (Pd), so as to disperse the active metal atoms and control the metal particle crystal phase exposition and shape for the catalyst. The different crystal phases of the noble metal in the catalyst are selectively exposed by controlling the molar ratio of concentration of the metal atoms to the concentration of the control ionic polymer within a preferred critical range of 1:0.5 to 1:5. Such ratio control is a critical factor the shape-control synthesis of the catalyst, because this ratio mainly determines the growing of different crystal phases of the metal atoms such as palladium on the support material. The growth rate of each crystal phase of the noble metal such as palladium is related to the number of control polymer molecules surrounding the palladium ion. A study showed that by using this control polymer method for making the catalyst, the resulting phase-controlled noble metal catalyst for reaction of hydrogen with oxygen-containing feedstreams improve the selectivity for hydrogen peroxide product up to about 100%. This is a significant improvement when compared to the selectivity of only about 64% for catalysts having uncontrolled Pd exposition under similar reaction conditions.

Tests have indicated that the supported noble metal phase controlled catalyst prepared according to this invention is active even with hydrogen-oxygen feedstreams containing only about 3.0 vol. % hydrogen, for advantageously producing hydrogen peroxide ($H_2O_2$) product at a selectivity exceeding 95% for a duration period of at least about 50 hours and probably much longer. Under similar process conditions, catalysts a prepared by other methods have been less active and exhibit lower selectivity for the hydrogen peroxide product. The support material useful in preparing catalysts made according to this invention are commercial available alumina, activated carbon with carbon black being preferred, carbon black, or silica which are widely available and have modest cost.

DESCRIPTION OF INVENTION

When hydrogen encounters oxygen, the thermodynamically favorable reaction product is water (equation 1). Hydrogen peroxide is an intermediate product and its further reaction within another hydrogen molecule leads to the formation of water (equations 2 and 3). Hydrogen peroxide is not a stable product, and upon its decomposition water and oxygen are released (equation 4).

$$2H_2 + O_2 = 2H_2O \tag{1}$$

$$H_2 + O_2 = H_2O_2 \tag{2}$$

$$H_2O_2 + H_2 = 2H_2O + O \tag{3}$$

$$2H_2O_2 = 2H_2O + O_2 \tag{4}$$

Because hydrogen peroxide is an intermediate product of the thermodynamically favorable reaction to water, it is critical to control catalytically the reaction between hydrogen and oxygen to selectively form the hydrogen peroxide precuts, otherwise water will be produced as the final product.

For a catalyst, an active noble metal such as palladium plays two critical roles during the reaction between hydrogen and oxygen feeds. Specifically, the palladium adsorbs molecular hydrogen and oxygen by its atoms exposed on the catalyst surface; and it helps the electron transfer between hydrogen and oxygen. As shown schematically in the upper row of FIG. 1, one hydrogen molecule and one oxygen molecule adsorb on the two palladium atoms adjacent to each other. The electro-negativity of oxygen tends to attract two electrons from hydrogen. However, the electron transfer from hydrogen to oxygen can be accomplished only through the palladium metal atoms due to its high electronic conductivity. After the electrons are transferred, an ionic action between $H_2^{2+}$ and $O_2^{2-}$ results in a hydrogen peroxide molecule. However, when two molecules of hydrogen and one molecule of oxygen are adsorbed on three adjacent palladium atoms, the transfer of electrons from hydrogen to oxygen will lead to the formation of two molecules of water (lower row of FIG. 1).

Figure 1:
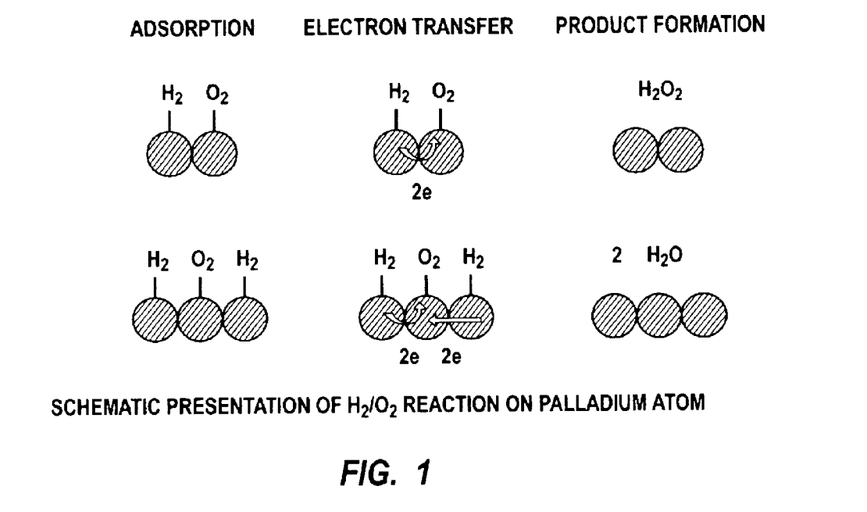
FIG. 1 is a schematic representation of various catalytic reactions of hydrogen and oxygen molecules with with active metal atoms of a catalyst for direct production of hydrogen peroxide ($H_2O_2$) product and water ($H_2O_2$)

As described above, the formation of hydrogen peroxide product needs the adsorption of one hydrogen molecule and one oxygen molecule on two adjacent palladium atoms. Meanwhile, the formation of water needs the adsorption of two hydrogen molecules and one oxygen molecule on three adjacent palladium atoms. It is expected that if an oxygen molecule is adsorbed on a palladium atom that is dispersed on the catalyst so as to have less adjacent palladium atoms, the probability of water formation is reduced. This means that if a catalyst surface is configured to expose less adjacent palladium atoms to a hydrogen-oxygen feedstream, the chance to catalyze water formation is much less than that catalyst surface which exposes more adjacent palladium atoms.

Figure 2:
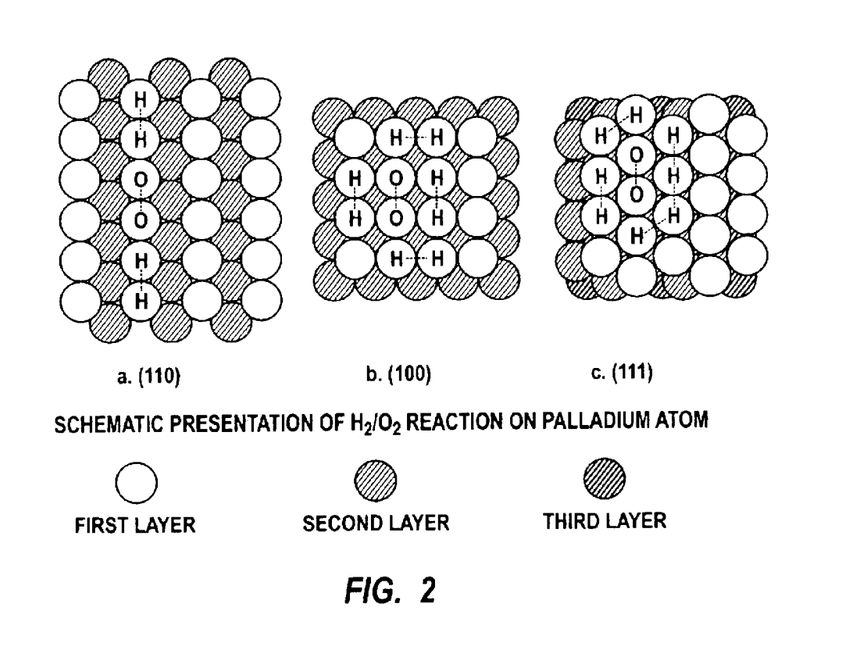
FIG. 2 shows a schematic comparative representation of different catalyst surface structures each having a different palladium (Pd) crystal phase, and the crystal phase 110 having a linear alignment of metal atoms on the crystals (FIG. 2a), which is considered most useful for the catalyst compared to the crystal phase 100 (FIG. 2b) and crystal phase 111 (FIG. 2c)

The surface structure of a catalyst having different crystal phases of active metal(s) such as palladium catalyst is shown schematically in FIG. 2. For phase 110 shown by FIG. 2a, each palladium atom has only two adjacent atoms; but there are more surrounding atoms on both the phase 100 (4 atoms) per FIG. 2b, and the phrase 111 (6 atoms) per FIG. 2c. The probability of undesired water formation on phase 110 is one third of that on phase 100, and one fifth of that on phase 111. Thus, for selective formation of hydrogen peroxide product, the catalyst must expose as much as possible of the Pd phase 110 or the similar phases 220, 300, 440 etc. Other Pd phases (100 and 111) provide the possibility of adsorbing several hydrogen molecules on the atoms adjacent to that adsorbed oxygen. Thus, the probability of water formation is significantly enhanced on these other Pd phases.

The exposition of each desired crystal phase or face of active noble metal such as palladium is principally controlled by the molar ratio of the palladium to a controlling polymer. It is also affected by other organo-metal solution properties such as pH, viscosity, ionic strength, and temperature. These parameters have been studied selectively to optimize the exposition of the desired palladium crystal phase. To achieve the high catalytic activity and selectivity for formation of hydrogen peroxide product, the noble metal and the control polymer such as palladium-polyacrylate precursor is dispersed on a support material having critical large surface area of 50–500 m²/g, such as activated carbon or carbon black. By utilizing this colloid precursor control procedure, the 0.1–10 wt. % noble metal is controllably deposited on the support material particles as a wide distribution of minute crystal sea having a size of 1–100 nm and so that at least some and preferably most of the noble metal crystals have a desired phase 110 and/or 220 exposition. The activity of selected phase—controlled noble metal catalysts is confirmed using a continuously stirred tank reactor (CSTR) system.

Catalyst Preparation Methods

For making the catalyst of this invention, a controlling precursor solution of an active noble metal and an ionic polymer is used to disperse atoms of the active noble metal component such as palladium on a support material having of 5–1000 μm and critical surface area of 50–500 m²g, such as carbon black. This method not only makes a catalyst having highly dispersed minute particles of active metal such as palladium on the support material, but also beneficially controls the exposition of the crystal phases of the palladium crystals on the support particles. The resulting catalyst has high activity which allows use of reduced safe hydrogen feed concentrations (below LEL 4.1%) in air. The selective exposition of different metal crystal phase(s) on the catalyst is critical for improvement in selectivity to form the hydrogen peroxide product, as the catalytic reaction is sensitive to the catalyst metal phase. The support materials useful in preparing the catalyst are commercially available alumina, activated carbon, carbon black, or silica which have modest cost within $1 to $5 per pound.

The catalysts of this invention are prepared by providing the controlling precursor solution which contains a dissolved noble metal salt such as palladium chloride and a negatively charged ionic water soluble control polymer having molecular weight of 300–8000, such as sodium polyacrylate having molecular weight of about 1200. Suitable control polymers should have a preferred molecular weight within the range of 600–6000 and be water soluble, and when combined with a salt of a selected noble metal such as palladium together with a minor amount of a platinum salt useful as an alloying agent and a support particles such as carbon black, will provide a desired alignment of the metal atoms so as to form crystals and provide metal particle size of 1–100 nm and phase control for the desired exposition of the metal crystals on the support. For palladium, a small percentage of a third metal salt dilute solution such as platinum chloride is added to form a metal alloy to reduce its solubility in the acid solution and prevent leaching of the active metal from the support.

For making the catalyst samples, the desired amount of palladium chloride (Pd $Cl_2$) was dissolved in a 0.4% hydrochloric acid (HCl) to form a first solution, and a second solution of the sodium polyacrylate in a aqueous solution was added to the first solution to provide a metal to ionic polymer molar ratio of 1:0.5–1:1.5. Then a third solution of platinum chloride solution was added to provide a palladium to platinum weight ratio in a range of 10:1 to 100:1. The combined solution was then purged with 100 ml/min nitrogen flow for 1 hour, and then reduced by 100 ml/min hydrogen for 20 minutes, and the palladium-sodium polyacrylate precursor solution is formed. The precursor material is missed with the selected carbon black catalyst support powder so that the support is impregnated with the precursor solution. After the catalyst sample was dried overnight, the metal was further reduced in hydrogen at temperature of 250–350° C. for 10–20 hours and the polymer removed, thereby leaving the metal crystal in a 100 and/or 220 phase exposition. The final catalyst should preferably have a palladium loading between about 0.5 to 0.7 wt. %.

The parameter that greatly affects the catalyst activity is the molar ratio of noble metal such as palladium to the control polymer, which ratio should preferably be between 1:0.5 and 1:5, and more preferably be in the range of 1:0.8 to 1:2. Desirable catalyst support materials may be selected form activated carbon or carbon black, and should have 5–1000 μm micrometers (μm) (nm) and total surface area of 140500 m²g, and preferably size μm and 200–450 m²g surface area.

Process for Hydrogen Peroxide Production

Figure 3:
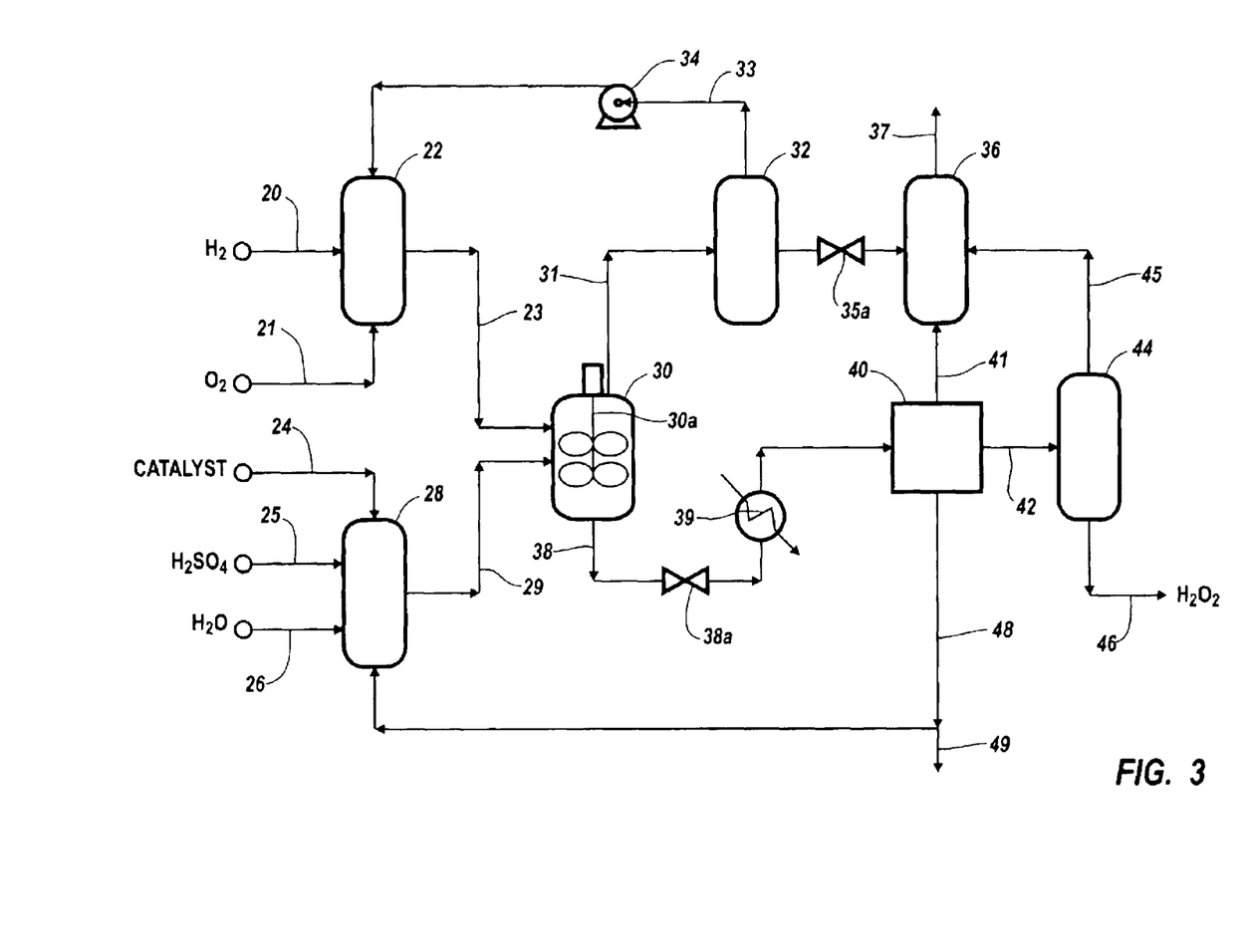
FIG. 3 shows a schematic flowsheet of a process for producing hydrogen peroxide ($H_2O_2$) product directly form gaseous hydrogen and oxygen feedstreams by utilizing the catalyst of this invention.

The catalyst material of this invention can be advantageously used in a process for direct catalytic production of hydrogen peroxide ($H_2O_2$) product from feedstreams of hydrogen and an oxygen-containing gas such as air. As shown in FIG. 3, the hydrogen gas feed is provided at 20, oxygen gas is provided at 21, the two feedstreams are each pressurized to reaction pressure and then premised together at mixer 22 so that the hydrogen is maintained below its explosive limit of 4.1 vol % in the mixed feedstream, and passed as mixed gas stream 23 into a stirred reactor 30 lined with glass or a suitable non-reactive polymer material. Also, the catalyst material in fine powder form is provided at 24, and acid such as sulfuric acid ($H_2SO_4$) is provided at 26, and all are pressurized and then mixed together in mixer 28 to form a catalyst-aqueous liquid slurry.

This aqueous liquid slurry from the mixer 28 is passed as stream 29 to the stirred reactor 30 in which the gas feed streams 23 and slurry liquid stream 29 are thoroughly mixed together at reaction conditions. Useful reaction conditions maintained in the reactor 30 are 0–80° C. temperature, 500–300 psig pressure and catalyst concentration of 1–40 gm catalyst/liter liquid for 0.2–6 hours residence time depending upon the mixing efficiency of the reactor, to produce a desired concentration of hydrogen peroxide product such as usually not exceeding about 20 vol %, with the product concentration being generally directly dependent on the reaction residing time. Preferred reaction conditions in reactor 30 are 30–50° C. temperature, 1000–200 psig pressure, catalyst concentration of 5–25 gm catalyst/liter, and 1–4 hours residence time in the reactor. Proper mixing of the gaseous feedstream 23 and liquid slurry feedstream 29 in the reactor 30 can be accomplished either by utilizing a mechanical stirrer device 30a, or by a liquid recycle system utilizing a recycle pump (not shown).

Form the reactor 30, a gas stream 31 is removed and passed to separator 32, from which a gas stream 33 containing dilute unreacted hydrogen and oxygen is recycled through compressor 24 back to the mixer 22. Also from separator 32, a purge gas stream 35 containing undesired inert gases is pressure-reduced at 35a and passed to a second mixer 36, from which gas stream 37 is vented to atmosphere.

Also from the reactor 30, a bottoms liquid stream 38 containing hydrogen peroxide and used catalyst is withdrawn, pressure-reduced at valve 38a, cooled at heat exchanger 39, and passed to a flash/filtration step at 40. Flashed gas is removed at 51 and passed to the mixer 36 while liquid removed at 42 is passed to a flash drum 44. From the flash drum 44, a desorbed vapor stream 45 is removed and also passed back to the mixer 36, from which a vent gas is disposed at 37 such as to a flare. Also from the flash drum 44, hydrogen peroxide liquid product is withdrawn at 46. Also from the gas/liquid/solids separation step at 40, used catalyst separated from the liquid such as by filtration is withdrawn at 48, and if desired can be recycled back to miser 28 for reuse in the process. After the catalyst age in the reactor 30 reaches at least about 50 hours and usually 100–300 hours and becomes less active, a minor portion of the used catalyst withdrawn at 48 can be discarded at 49 and replaced by an equivalent amount of fresh catalyst at 24 to maintain desired high activity of the catalyst in the stirred reactor 30.

This invention will be described further by use of the following examples, which should not be construed as limiting the scope of the invention.

EXAMPLE NO. 1

Several experimental screening runs were made with catalyst samples made utilizing various support materials to determine desired characteristic of effective support materials for an improved supported palladium catalyst useful for the direct production of hydrogen peroxide ($H_2O_2$) from hydrogen and oxygen feedstreams. The screening runs for the catalyst samples made in a stirred glass lined one-liter capacity autoclave unit, using as feed bases 1.9% hydrogen in air at reaction conditions of 350° C. temperature and 1000 psig pressure, with catalyst concentration of 10 grams catalyst per liter of liquid at feed gas rate of 1 liter/minute for 3 hours duration. The results are shown in Table 1 below.

TABLE 1

Catalyst Performance on Different Supports

| Support No. | Support Material | Surface Area $m^2/g$ | $H_2O_2$ concentration wt. % |
|---|---|---|---|
| 1 | Carbon black | 1,500 | 0.1 |
| 2 | Activated carbon | 1,200 | 0 |
| 3 | Activated carbon | 1,000 | 0 |
| 4 | Activated alumina | 325 | 0.1 |
| 5 | Activated alumina | 200 | 0.3 |
| 6 | Carbon black | 200 | 1.6 |
| 7 | Carbon black | 140 | 1.4 |

From these results, it is seen that the support materials having surface area of 1000 m/²g or greater were inactive, apparently because of pore sizes being too small so the water condensation prevents hydrogen and oxygen gas from reaching the palladium active sites. Also, the catalyst samples supported on activated alumina did not provide good activity for hydrogen peroxide production, apparently because of interaction of palladium with the alumina provided weak adsorption of oxygen. The catalyst samples with carbon black support material having 140–200 m²/g surface area provided the most effective support material for the catalyst.

EXAMPLE NO. 2

Because the molar ratio of palladium to the control ionic polymer sodium polyacrylate used in making the catalyst greatly affects catalyst activity, additional experimental runs were made using the carbon black catalyst support No. 6 from Example No. 1 to determine the effect of different ratios of palladium (Pd) to the control polymer for making the catalyst. These runs were made at reaction conditions of 45° C. temperature, 1,000 psig pressure, and 10 gm catalyst concentration per liter of liquid, at feed rate of 1 liter/minute of feed gas containing 3.0% hydrogen in air. The results are shown in Table 2 below.

TABLE 2

Effect of Pd to Polymer Ratio on Catalyst Activity

| Pd/Polymer Molar Ratio | $H_2O_2$ Concentration wt. % | $H_2O_2$ Selectivity wt. % |
|---|---|---|
| 1:0.5 | 2.7 | 63 |
| 1:1.0 | 3.3 | 93 |
| 1:2.5 | 0.2 | — |
| 1:5.0 | 0 | — |

From these results, it is seen that a catalyst utilizing a molar ratio of palladium to the sodium polyacrylate polymer of about 1:1 provided the best hydrogen peroxide product concentration selectivity.

EXAMPLE NO. 3

Other experimental runs were made at the reaction conditions of Example No. 2 on a catalyst having support No. 6 from Table 1 to determine the effect of catalyst concentration in the stirred one-liter capacity on $H_2O_2$ product selectivity and yield. The results are shown in Table 3 below.

TABLE 3

Effect of Catalyst Concentration in Medium

| Catalyst Concentration, g/liter | $H_2$ Conversion, wt. % | $H_2O_2$ Concentration, wt. % | $H_2O_2$ Selectivity, wt. % | $H_2O_2$ Yield, g/gPd/h |
|---|---|---|---|---|
| 5 | 7 | 1.1 | 100 | 124 |
| 10 | 15 | 2.3 | 100 | 131 |
| 20 | 24 | 2.9 | 83 | 83 |

From the above results, it is seen that hydrogen peroxide yield increased with increase catalyst concentration in the stirred reactor up to about 10 g/liter of liquid, while maintaining the product selectivity at 100%. But at higher catalyst concentration the hydrogen peroxide selectivity and yield decreased, apparently because too much catalyst in the reactor causes further oxidation of the hydrogen peroxide to form undesired water. Catalyst concentration in the stirred reactor of 5–10 gm catalyst/liter yielded the best results of product concentration, selectivity and yield.

EXAMPLE NO. 4

Another series of experimental runs were made to determine the reaction conditions which product the best product results. Runs were made at reaction temperatures of 35° C., 45° C. and 55° C. and at pressures of 1000–1800 psig. With 10 gm catalyst/liter concentration in the reactor 3 hour duration. The results are presented in Tables 4 and 5 below.

TABLE 4

Effect of Reaction Temperature

| Temperature ° C. | $H_2$ Conversion, wt. % | $H_2O_2$ Concentration, wt. % | $H_2O_2$ Selectivity, wt. % | $H_2O_2$ Yield, g/gPd/h |
|---|---|---|---|---|
| 35 | 15 | 2.3 | 100 | 131 |
| 45 | 25 | 3.3 | 93 | 189 |
| 55 | 38 | 3.8 | 71 | 219 |

TABLE 5

Effect of Reaction Pressure

| Pressure, Psig | $H_2$ Conversion, wt. % | $H_2O_2$ Concentration, wt. % | $H_2O_2$ Selectivity, wt. % | $H_2O_2$ Yield, g/gPd/h |
|---|---|---|---|---|
| 1000 | 25 | 3.3 | 93 | 189 |
| 1400 | 33 | 4.8 | 100 | 279 |
| 1800 | 34 | 5.2 | 100 | 304 |

From the above results, it is noted that while the hydrogen peroxide product yield increased temperature due to increased catalytic activity, the product selectivity decrease because the hydrogen peroxide began decomposing to form undesired water. Also increased reaction pressure apparently increases solubility of the reactant gases and improved ass transfer to the catalyst active sites. Thus, the best operating conditions for the stirred reactor were at 35–45° C. temperature and 1400–1800 psig pressure or catalyst on of 5–10 gm/liter and about 3 hour duration.

EXAMPLE NO. 5

Further experimental runs were made in the stirred one liter capacity autoclave unit at 2, 3 and 6 hours duration evaluate reaction time duration for each batch. Although longer action time accumulates the hydrogen peroxide product to greater concentrations, extended product exposure to the catalyst can result in over oxidation to form undesired water. The reaction time duration results are presented in Table 6 below.

TABLE 6

Effect of Reaction Time for Each Batch

| Reaction Time, hour | $H_2$ Conversion, wt. % | $H_2O_2$ Concentration, wt. % | $H_2O_2$ Selectivity, wt. % | $H_2O_2$ Yield, g/pPd/h |
|---|---|---|---|---|
| 2 | 31 | 2.9 | 100 | 249 |
| 3 | 33 | 4.8 | 100 | 279 |
| 6 | 34 | 9.1 | 99 | 276 |

From results, it is seen that the catalyst has high selectivity for hydrogen peroxide product, and its concentration and yield increased up to about 6 hours time duration in the autoclave reactor with no significant decomposition of the hydrogen peroxide product.

EXAMPLE NO. 6

Figure 4:
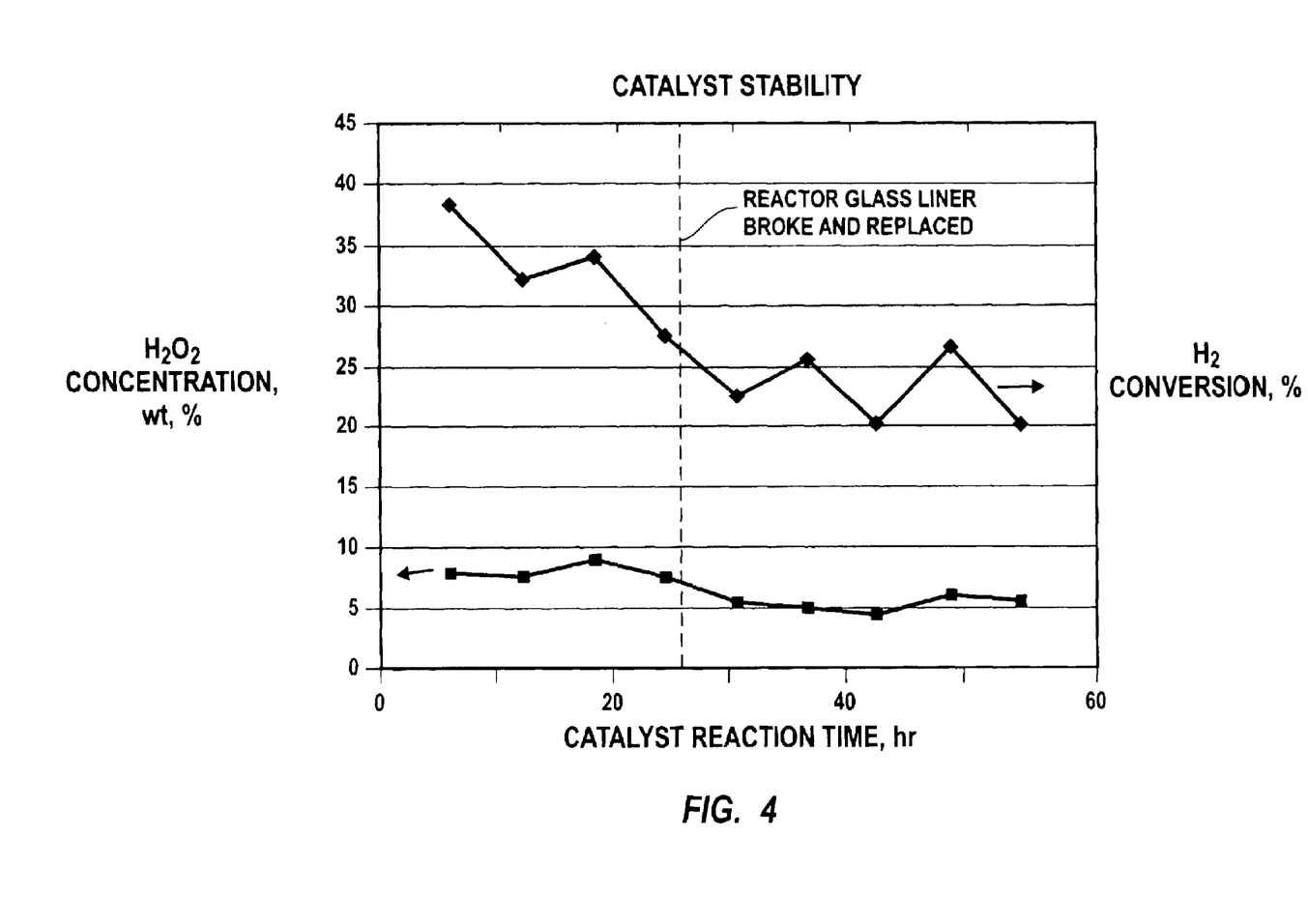
FIG. 4 is a graph showing percent hydrogen conversion and hydrogen peroxide concentration plotted vs. reaction time duration for the catalyst in a stirred catalytic reactor.

A simulated catalyst stability test was performed on catalyst having support No. 6 in Table 1, using the stirred autoclave nit at the conditions of Example 2. Because the reactor liquid phase was not a continuous flow mode as would be utilized in a commercial process, the reaction was topped at successive 6-hour intervals and the hydrogen peroxide concentration of the reactor liquid was determined by analyses. During the fifth such test the autoclave reactor glass liner was inadvertently broken, which resulted in contamination of the catalyst by exposure to dissolved metal ions from the stainless steel reactor, as it is known that exposure to Cr and Fe favors decomposition of hydrogen peroxide. Results of this catalyst stability test during nine successive 6-hour runs is shown in FIG. 4, in which percent hydrogen conversion and hydrogen peroxide concentration are plotted vs. reaction time duration in the reactor.

From these results, it is noted that the hydrogen conversion declined somewhat during the first four 6-hour run intervals and they hydrogen peroxide concentration remained essentially constant at about 8 wt. % for 4 hours duration. For the final five 6-hour runs, the hydrogen peroxide product concentration remained generally constant at 5–6 wt. % for an additional 30 hours duration. Based on these data, it appears that the catalyst activity remained generally constant for a total of about 56 hours. Thus the hydrogen conversion and hydrogen peroxide concentration data indicate that the catalyst useful life is at least about 56 hours, and is probably significantly longer such as up to about 500 hours.

Although this invention has been described broadly and also in terms of preferred catalyst composition, method for making the catalyst and process reaction conditions, it is within the scope as defined by the claims.

What is claimed is:

1. A supported noble metal catalyst, comprising:
   a particulate support material; and
   at least one noble metal controllably deposited on said particulate support material as widely distributed noble metal crystal particles,
   at least a majority of said noble metal crystal particles having a 110 and/or 220 phase exposition so that at least a majority of active surface atoms of the noble metal crystal particles are exposed in an orderly pattern characteristic of the 110 and/or 220 phase exposition.

2. A supported noble metal catalyst as defined in claim 1, said particulate support material having a particle size in a range of 5–1,000,000 nm.

3. A supported noble metal catalyst as defined in claim 1, said particulate support material having a particle size in a range of 15–5,000 nm.

4. A supported noble metal catalyst as defined in claim 1, said particulate support material having a total surface area in a range of 50–500 m$^2$/g.

5. A supported noble metal catalyst as defined in claim 1, said particulate support material comprising carbon black having total surface in a range of 100–250 m$^2$/g.

6. A supported noble metal catalyst as defined in claim 1, said support material comprising at least one member selected from the group comprising alumina, activated carbon, carbon black, and silica.

7. A supported noble metal catalyst as defined in claim 1, said noble metal having a concentration in a range of 0.1–10 wt. %.

8. A supported noble metal catalyst as defined in claim 1, said noble metal having a concentration in a range of 0.2–5 wt %.

9. A supported noble metal catalyst as defined in claim 1, said noble metal comprising at least one member selected from the group comprising palladium, platinum, gold, iridium, osmium, rhodium, and ruthenium.

10. A supported noble metal catalyst as defined in claim 1, said noble metal comprising an alloy of two or more noble metals.

11. A supported noble metal catalyst as defined in claim 10, said alloy comprising palladium and at least one other noble metal.

12. A supported noble metal catalyst as defined in claim 11, said other noble metal in said alloy comprising at least one of gold, iridium, osmium, rhodium, or ruthenium.

13. A supported noble metal catalyst as defined in claim 11, said other noble metal in said alloy comprising platinum.

14. A supported noble metal catalyst as defined in claim 13, said noble metal alloy having a palladium to platinum weight ratio in a range of 20:1 to 100:1.

15. A supported noble metal catalyst as defined in claim 1, said noble metal crystal particles having a size in a range of 1–100 nm.

16. A supported noble metal catalyst as defined in claim 1, substantially all of said noble metal crystal particles having a 110 and/or 220 phase exposition so that substantially all of the active surface atoms of said noble metal crystal particles are exposed in an orderly pattern characteristic of the 110 and/or 220 phase exposition.

17. A supported noble metal catalyst as defined in claim 1, said catalyst being suitable for use in the direct catalytic production of hydrogen peroxide ($H_2O_2$) from hydrogen- and oxygen-containing feedstreams.

18. A method of catalytically producing hydrogen peroxide from hydrogen and oxygen-containing feedstreams, comprising:
   (a) providing a gaseous feedstream comprising hydrogen gas and oxygen;
   (b) foaming an aqueous liquid slurry comprising the supported noble metal catalyst of claim 1; and
   (c) reacting the aqueous liquid slurry with the gaseous feedstream to yield hydrogen peroxide.

19. A method of catalytically producing hydrogen peroxide as defined in claim 18, the gaseous feedstream being continuously introduced into a reactor containing the aqueous liquid slurry and the hydrogen being withdrawn continuously.

20. A method of catalytically producing hydrogen peroxide as defined in claim 18, said supported noble catalyst comprising palladium.

21. a method of catalytically producing hydrogen peroxide as defined in claim 20, said supported noble metal catalyst further comprising platinum.

22. A supported noble metal catalyst, comprising:
   a particulate support material; and
   at least one noble metal controllably deposited on said particulate support material so as to provide a wide distribution of minute noble metal crystal particles having a particle size in a range of 1–100 nm,
   said noble metal comprising palladium,
   at least a majority of said noble metal crystal particles having a 110 and/or 220 phase exposition so that at least a majority of active surface atoms of the noble metal crystal particles are exposed in an orderly pattern characteristic of the 110 and/or 220 phase exposition.

23. A supported noble metal catalyst as defined in claim 22, said noble metal further comprising at least one other noble metal in addition to palladium.

24. A supported noble metal catalyst as defined in claim 23, said noble metal further comprising platinum as an alloying agent.

25. A supported noble metal catalyst as defined in claim 22, substantially all of said noble metal crystal particles having a 110 and/or 220 phase exposition so that substantially all of the active surface atoms of said noble metal crystal particles are exposed in an orderly pattern characteristic of the 110 and/or 220 phase exposition.

26. A method of making a supported noble metal catalyst, comprising:
   (a) providing a first solution containing at least one noble metal salt;
   (b) providing a second solution comprising at least one ionic control polymer dissolved in water, said control polymer having molecular weight in a range of 300–8000;

(c) mixing said first and second solutions together so as to form a precursor solution in which the molar ratio of said noble metal salt to said control polymer is in a range of 1:0.1 to 1:10;

(d) mixing said precursor solution with a particulate support material so as to impregnate said particulate support material with said precursor solution;

(e) drying said impregnated particulate support material; and (f) removing said control polymer to yield a supported noble metal catalyst comprising active minute noble metal crystal particles in which at least a majority have a phase exposition of 110 and/or 220 so that at least a majority of active surface atoms of the noble metal crystal particles are exposed in an orderly pattern characteristic of the 110 and/or 220 phase exposition.

27. A method of making a supported noble metal catalyst as defined in claim 26, said first solution comprising palladium chloride and said second solution comprising sodium polyacrylate.

28. A method of making a supported noble metal catalyst as defined in claim 27, said first solution further comprising a dilute acid.

29. A method of making a supported noble metal catalyst as defined in claim 27, further comprising mixing a third solution comprising a platinum salt with said first and second solutions before mixing said precursor solution with said particulate support material.

30. A method of making a supported noble metal catalyst as defined in claim 29, said platinum salt comprising hydrogen hexachloroplatinate ($H_2PtCl_6$) in an amount so us to provide a palladium to platinum weight ratio in a range of 20:1 to 100:1.

31. A method of making a supported noble metal catalyst as defined in claim 26, said control polymer having a molecular weight in a range of 600–6000.

32. A method of making a supported noble metal catalyst as defined in claim 26, said control polymer comprising a polyacrylate.

33. A method of making a supported noble metal catalyst as defined in claim 26, said control polymer comprising at least one member selected from the group comprising polyvinyl benzoates, polyvinyl sulfates, polyvinyl sulfonates, polybiphenol carbonates, polybenzimidozoles, and polypyridines.

34. A method of making a supported noble metal catalyst as defined in claim 26, the molar ratio of said noble metal salt to said control polymer in said precursor solution is in a range of 1:0.5 to 1:5.

35. A method of making a supported noble metal catalyst as defined in claim 26, the molar ratio of said noble metal salt to said control polymer in said precursor solution is in a range of 1:0.8 to 1:2.

36. A method of making a supported noble metal catalyst as defined in claim 26, said particulate support material having a surface area in a range of 50 . 500 m²/g.

37. A method of making a supported noble metal catalyst as defined in claim 26, further comprising reducing the precursor solution obtained in (c) with hydrogen.

38. A method of making a supported noble metal catalyst as defined in claim 26, removing said control agent in (f) being performed by reducing the supported noble metal catalyst with hydrogen.

39. A method of making a supported noble metal catalyst as defined in claim 26, said supported noble metal catalyst being suitable for use in the direct catalytic production of hydrogen peroxide ($H_2O_2$) from hydrogen- and oxygen-containing feedstreams.

40. A method of making a supported noble metal catalyst as defined in claim 26, wherein (f) yields a supported noble metal catalyst in which substantially all of said noble metal crystal particles have a 110 and/or 220 phase exposition.

41. A method of making a supported palladium catalyst, comprising:

(a) providing a first solution comprising a palladium salt;

(b) providing a second solution comprising a polyacrylate;

(c) mixing said first and second solutions together so as to form a precursor solution in which the molar ratio of said palladium salt to said polyacrylate is in a range of 1:0.5 to 1:5;

(d) mixing the precursor solution with a particulate support material so as to impregnate said particulate support material with said precursor solution;

(e) drying said impregnated particulate support material; and (f) reducing said impregnated particulate support material with hydrogen gas to yield a supported palladium catalyst comprising active minute palladium crystals in which at least a majority have a phase exposition of 110 and/or 220 so that at least a majority of active surface atoms of the palladium crystal particles are exposed in an orderly pattern characteristic of the 110 and/or 220 phase exposition.

42. A method of making a supported noble metal catalyst as defined in claim 18, said first solution further comprising a dilute acid.

43. A method of making a supported palladium catalyst as defined in claim 41, further comprising adding a platinum salt to the precursor solution.

44. A method of making a supported noble metal catalyst as defined in claim 41, further comprising reducing the precursor solution obtained in (c) with hydrogen.

45. A method of making a supported noble metal catalyst as defined in claim 41, the molar ratio of said palladium salt to said polyacrylate in said precursor solution is in a range of 1.0.8 to 1:2.

46. A method of making a supported noble metal catalyst as defined in claim 41, wherein (f) yields a supported noble metal catalyst in which substantially all of said noble metal crystal particles have a 110 and/or 220 phase exposition.

* * * * *

UNITED STATES PATENT AND TRADEMARK OFFICE
CERTIFICATE OF CORRECTION

PATENT NO. : 6,919,065 B2  Page 1 of 4
APPLICATION NO. : 10/431693
DATED : July 19, 2005
INVENTOR(S) : Bing Zhou and Lap-Keung Lee It is certified that error appears in the above-identified patent and that said Letters Patent is hereby corrected as shown below:

Cover Page
Item [57], ABSTRACT, line 2, after "having" insert --a particle size of--
Item [57], ABSTRACT, line 2, after "5–1000 μm" insert --and a--
Item [57], ABSTRACT, lines 2 and 3, change "50μ500 m$^2$/gm" to
--50–500 m$^2$/gm--

Drawings
Sheet 2, Replace Figure 3 with the figure depicted herein below, wherein reference numeral --35-- has been added. (see attached)

FIG. 3

Column 1
Line 58, after "product can" change "e" to --be--

UNITED STATES PATENT AND TRADEMARK OFFICE
CERTIFICATE OF CORRECTION

PATENT NO. : 6,919,065 B2
APPLICATION NO. : 10/431693
DATED : July 19, 2005
INVENTOR(S) : Bing Zhou and Lap-Keung Lee It is certified that error appears in the above-identified patent and that said Letters Patent is hereby corrected as shown below:

Column 3
Line 35, change "metal s" to --metals--
Line 40, change "charge" to --charged--
Line 41, change "charge" to --charged--
Line 50, change "weigh to" to --weight--

Column 4
Line 28, change "commercial" to --commercially--
Line 36, remove the second instance of "with"
Line 38, after "water" change "($H_2O_2$)" to --($H_2O$)--
Line 47, change "form" to --from--

Column 5
Line 45, change "phrase" to --phase--

Column 6
Line 39, before "support particles" remove "a"
Line 54, after "platinum chloride" remove "solution"
Line 63, before "temperature" insert --a--
Line 65, change "100" to --110--

Column 7
Line 6, change "form" to --from--
Line 6, after "have" insert --a particle size of--
Line 7, remove "(nm)"
Line 8, change "140500 $m^2g$" to --140–500 $m^2/g$--
Line 8, after "200–450" change "$m^2g$" to --$m^2/g$--
Line 22, after "24," insert --water at 26,--
Line 23, change "26" to --25--
Line 45, change "Form" to --From--
Line 48, change "24" to --34--
Line 56, change "51" to --41--

Column 8
Line 15, change "characteristic" to --characteristics--
Line 22, change "350°C" to --35°C--
Line 41, change "$m/^2g$" to --$m^2/g$--

UNITED STATES PATENT AND TRADEMARK OFFICE
CERTIFICATE OF CORRECTION

PATENT NO. : 6,919,065 B2
APPLICATION NO. : 10/431693
DATED : July 19, 2005
INVENTOR(S) : Bing Zhou and Lap-Keung Lee It is certified that error appears in the above-identified patent and that said Letters Patent is hereby corrected as shown below:

Column 9
Line 51, change "product" to --produce--

Column 10
Line 15, change "decrease" to --decreased--
Line 18, change "ass" to --gas--
Line 27, before "evaluate" insert --to--
Line 54, change "nit" to --unit--

Column 11
Line 3, change "they" to --the--

Column 13
Line 56, change "50 . 500" to --50–500--

Column 14
Line 40, change "claim 18" to --claim 41--
Line 51, change "1.0.8" to --1:0.8--

Signed and Sealed this

Seventeenth Day of October, 2006

JON W. DUDAS
*Director of the United States Patent and Trademark Office*

FIG. 3

UNITED STATES PATENT AND TRADEMARK OFFICE
CERTIFICATE OF CORRECTION

PATENT NO. : 6,919,065 B2  Page 1 of 1
APPLICATION NO. : 10/431693
DATED : July 19, 2005
INVENTOR(S) : Bing Zhou and Lap-Keung Lee It is certified that error appears in the above-identified patent and that said Letters Patent is hereby corrected as shown below:

<u>Column 14</u>
Line 39, change "noble metal" to --palladium--
Line 45, change "noble metal" to --palladium--
Line 48, change "noble metal" to --palladium--
Line 52, change "noble metal" to --palladium--

Signed and Sealed this

Fourteenth Day of November, 2006

JON W. DUDAS
*Director of the United States Patent and Trademark Office*